United States Patent
Amato (10) Patent No.: US 11,278,380 B2
(45) Date of Patent: Mar. 22, 2022

(54) METHOD FOR DETERMINING AND DRAWING THE IDEAL INDIVIDUAL SHAPE OF THE UPPER FRONT TEETH

(71) Applicant: Aldo Amato, Borgoricco (IT)

(72) Inventor: Aldo Amato, Borgoricco (IT)

(*) Notice: Subject to any disclaimer, the term of this patent is extended or adjusted under 35 U.S.C. 154(b) by 538 days.

(21) Appl. No.: 16/323,695

(22) PCT Filed: Sep. 5, 2017

(86) PCT No.: PCT/IB2017/055327
§ 371 (c)(1),
(2) Date: Feb. 6, 2019

(87) PCT Pub. No.: WO2018/025251
PCT Pub. Date: Feb. 8, 2018

(65) Prior Publication Data
US 2019/0201170 A1    Jul. 4, 2019

(51) Int. Cl.
| | | |
|---|---|---|
| *A61C 9/00* | (2006.01) | |
| *A61C 13/00* | (2006.01) | |
| *A61C 19/04* | (2006.01) | |
| *A61C 13/08* | (2006.01) | |
| *A61B 5/00* | (2006.01) | |

(52) U.S. Cl.
CPC ........ *A61C 9/0053* (2013.01); *A61C 13/0004* (2013.01); *A61C 13/082* (2013.01); *A61C 19/04* (2013.01); *A61B 5/4547* (2013.01)

(58) Field of Classification Search
CPC . A61C 9/0053; A61C 13/0004; A61C 13/082; A61C 19/04; A61B 5/4547
See application file for complete search history.

(56) References Cited

U.S. PATENT DOCUMENTS

| | | | |
|---|---|---|---|
| 8,092,220 B2* | 1/2012 | Wiedmann | A61C 13/082 433/202.1 |
| 8,406,908 B2* | 3/2013 | Monkmeyer | A61C 13/0004 700/98 |
| 8,423,335 B2* | 4/2013 | Methot | A61C 13/0004 703/6 |
| 8,706,672 B2* | 4/2014 | Malfliet | G06T 7/0012 706/47 |
| 9,336,336 B2* | 5/2016 | Deichmann | A61C 5/77 |
| 9,411,910 B2* | 8/2016 | Methot | G16H 20/40 |
| 9,642,686 B1* | 5/2017 | Kalman | A61C 13/34 |
| 10,896,761 B2* | 1/2021 | Stone-Collonge | A61C 7/002 |
| 11,024,431 B2* | 6/2021 | Stone-Collonge | A61B 5/0077 |
| 2010/0049351 A1* | 2/2010 | Monkmeyer | A61C 5/77 700/98 |
| 2010/0145898 A1* | 6/2010 | Malfliet | G06T 7/0012 706/47 |

(Continued)

FOREIGN PATENT DOCUMENTS

| | | |
|---|---|---|
| WO | 2008031614 | 3/2008 |
| WO | 2011062473 | 5/2011 |

(Continued)

*Primary Examiner* — Nicholas D Lucchesi (74) *Attorney, Agent, or Firm* — Themis Law (57) ABSTRACT

A method for determining and drawing the ideal individual shape of the two front upper teeth uses at least one image of the patient's face in front view, non-smiling and with the mouth closed, and at least one image of the patient's face in front view, smiling and with closed teeth.

10 Claims, 6 Drawing Sheets

(56) References Cited

U.S. PATENT DOCUMENTS

| | | | |
|---|---|---|---|
| 2012/0010533 A1* | 1/2012 | Arnett | G06K 9/00281 |
| | | | 600/590 |
| 2013/0218530 A1* | 8/2013 | Deichmann | A61C 5/77 |
| | | | 703/1 |
| 2015/0379780 A1* | 12/2015 | Jin | G06T 17/00 |
| | | | 345/419 |
| 2018/0125610 A1* | 5/2018 | Carrier, Jr | A61C 19/04 |
| 2018/0235729 A1* | 8/2018 | Kim | A61C 7/002 |

FOREIGN PATENT DOCUMENTS

| | | |
|---|---|---|
| WO | 2012006717 | 1/2012 |
| WO | 2016055890 | 4/2016 |

* cited by examiner

METHOD FOR DETERMINING AND DRAWING THE IDEAL INDIVIDUAL SHAPE OF THE UPPER FRONT TEETH

This patent relates to the methods of tooth reconstruction and in particular relates to a new method to determine and draw the ideal individual shape of the two upper front teeth, depending on the shape of the patient's face.

Prior art includes different methods to determine the shape of missing, broken, or damaged teeth of a patient using parameters determined by measurements made on the face and/or teeth of the patient.

For example, the patent document U.S. Pat. No. 8,092,220 introduces a method for the reconstruction of missing, broken or damaged teeth by way of an analysis of the patient's face. In particular, in order to determine the shape and size of a tooth, the face of the patient for whom the tooth is intended is analyzed using one or more photographs of the face and where the obtained values serve to determine proportionally the actual shape and size of the tooth.

Specifically, the method includes the determination of the width of the nose, measured at its base, to determine the ideal distance between the tips of the two upper canines. The length obtained in this manner is subdivided proportionally to determine the width of the four upper incisors.

In contrast the shape of the teeth is designed on the basis of other parameters. For example, the shape of the two central incisors is designed on the base reproducing the contour of the face, rotated 180°.

The present application concerns a new method to determine and design the ideal individual shape of the two upper front teeth.

The new method differs from the aforementioned document and other known methodologies, allowing the determination of a number of ideal points to redesign the two upper front teeth, where these ideal points are derived from the patient's facial parameters, original teeth, and statistical parameters.

The new method can be included in an algorithm, to be used for the development of dedicated software applications.

The new method involves the use of at least one digital image of the patient's face, with frontal view and closed mouth with no smile, and at least one digital image of the same face, frontal view with a smile and clenched teeth.
Determination of the Shape of the Upper Center Incisor, Right or Left.

For clarity, reference is made to the attached drawings, by way of a non-limiting example.

By way of a non limiting example, consider the determination of the shape of the upper right central incisor (11), where the method to determine the shape of the upper left central incisor (21) is repeated in the form of a mirror image.

The method comprises the following steps:

A) Determination of the front facial angle (AFF) of the patient's face, from a photo of the patient's face with closed mouth and no smile.

According to a first method, the determination of the front facial angle (AFF) is known from patent application WO2016055890, by the same applicant.

Figure 1:
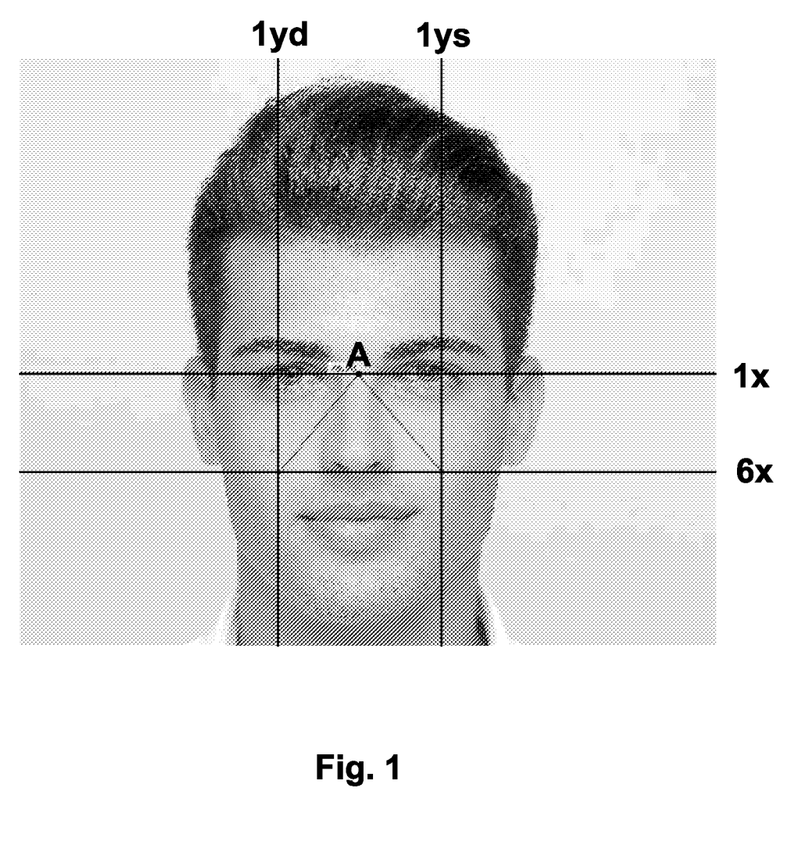
FIG. 1 shows a frontal image of the patient who is smileless with closed mouth, on which the structure to determine the front facial angle (AFF) is indicated.

According to a further method, with reference to FIG. 1 showing an image of a face in frontal view and with mouth closed and no smile, the front facial angle (AFF) is the angle between the segments joining at the vertex in correspondence to the nasion (A) and which intersect the points (H, B) of intersection between the horizontal line ($6x$) passing through the nasal spine (N) and two vertical lines ($1yd$, $1ys$) passing through the distal irides respectively right and left.

B) Construction of a parabola on the picture of the patient's face with closed mouth and no smile.

Figure 2:
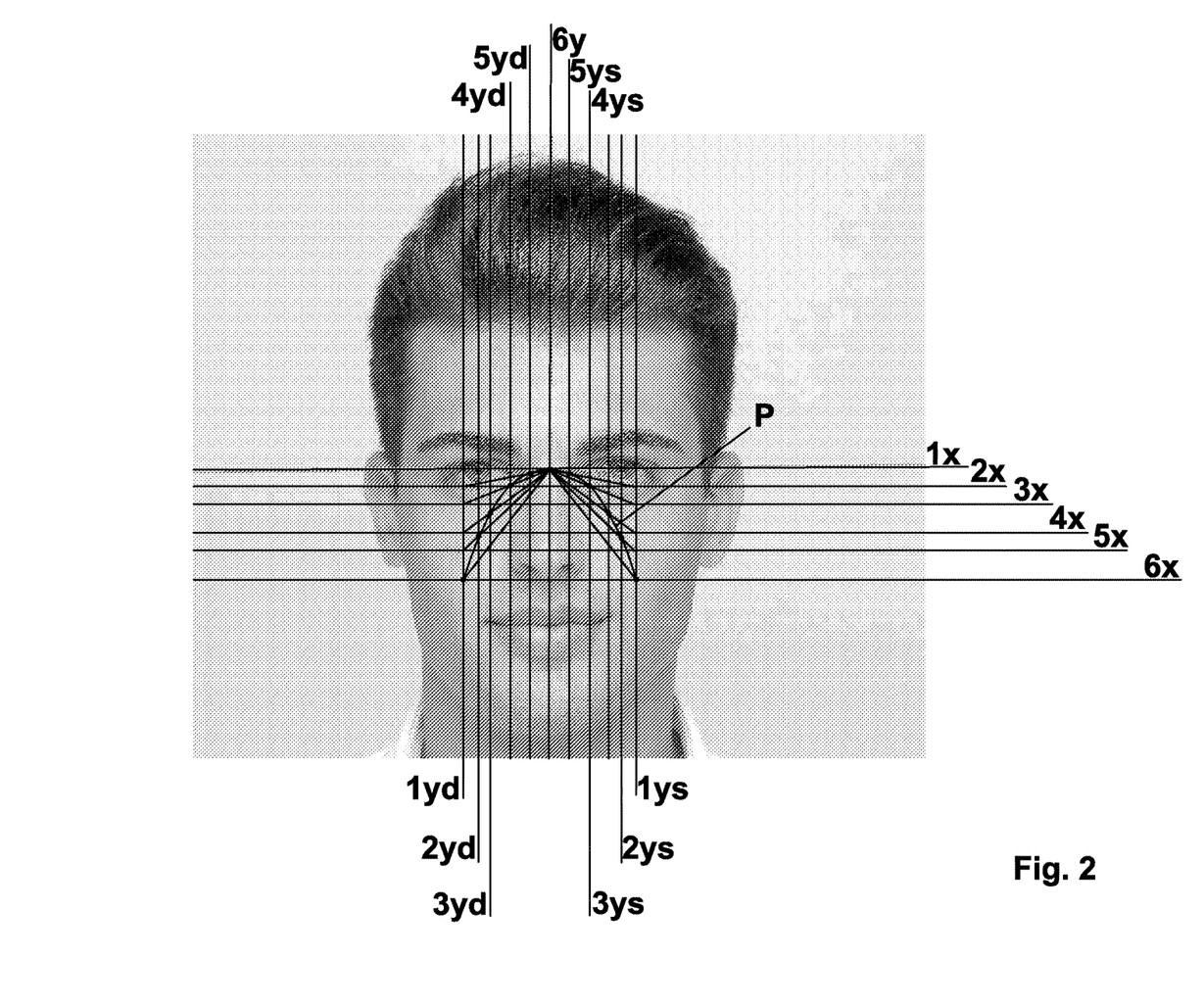
FIG. 2 shows a frontal image of the patient who is smileless with closed mouth, on which the structure to determine the parabola of the face (P) is indicated, used to draw the gingival parabola (HAB).

With reference to FIG. 2, step B) requires:

1) Draw the following vertical lines:
the vertical median line of the face ($6y$), passing through the trichion (T), the nasion (A) and the menton (M);
the line passing through the right medial canthus ($4yd$);
the line passing through the mesial point of the right iris ($3yd$);
the line passing through the right pupil ($2yd$);
the line passing through the distal point of the right iris ($1yd$);
the line passing through the left medial canthus ($4ys$);
the line passing through the mesial point of the left iris ($3ys$);
the line passing through the left pupil ($2yd$);
the line passing through the distal point of the left iris ($1yd$);
two lines passing through the median points of the segment between the nasion (A) and the right and left medial canthuses ($5yd$, $5ys$) and the following horizontal lines:
line passing through the pupils ($1x$);
line passing through the point corresponding to the nasal spine ($6x$)
four horizontal lines ($2x$, $3x$, $4x$, $5x$) comprised between those two horizontal lines ($1x$, $6x$) defined above, so that the horizontal lines ($1x$, $2x$, $3x$, $4x$, $5x$, $6x$) are spaced apart respectively 16%, 16%, 26%, 16%, 26% of the interval between the extreme horizontal lines ($1x$, $6x$).

2) Connect the point on the nasion (A) with the intersection points between the vertical lines ($1yd$, $1ys$) passing through the distal points on the irises and the five horizontal lines ($2x$, $3x$, $4x$, $5x$) below the horizontal line passing through the pupils ($1x$).

3) Highlight the intersection points between the ten oblique lines obtained, on the right and left, and the vertical lines ($1yd$-$6yd$) and ($1ys$-$6ys$).

4) Draw a parabola with vertex at A and base at H and B, passing through the points highlighted above.

Figure 3:
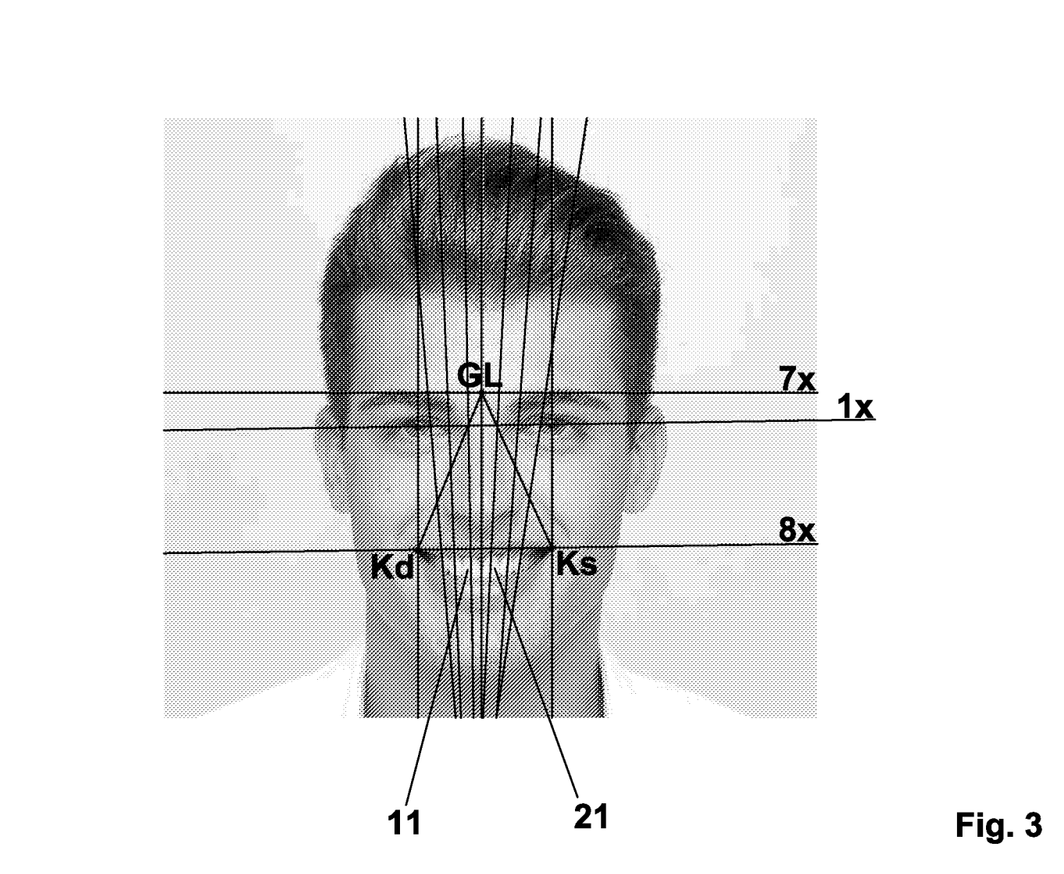
FIG. 3 shows the frontal image with a smile and clenched teeth, on which the structure to determine the correct orientation of the parabola as a function of the gingival zeniths is indicated.

C) Orientation of the parabola according to the ideal individual gingival zeniths obtained from the following method and from a frontal image of the patient's face with smile and clenched teeth:

1) With reference to FIG. 3, draw the right and left vertical lines passing through the pupils (2yd, 2ys), and the vertical median line (6y).

2) Draw horizontal lines passing through the glabella (7x), pupils (1x), and left and right chelion (8x).

3) Draw the diagonal lines with vertex (GL) at the point of intersection between the horizontal line passing through the glabella (7x) and the vertical median line (6x), the diagonal lines passing through the right and left chelions (Kd, Ks).

4) Draw the medians of the upper front teeth affecting the smile area (four, six, or eight), determined on the basis of an ideal frontal width determined by the professional user or other dedicated computer applications, and highlight the points on these medians of the teeth at the level of the incisal margin of the incisors or on the cusps of the canines and the first premolars, if visible.

5) Draw the lines (1d, 2d, 3d, 4d, 1s, 2s, 3s, 4s) that pass through these points of the teeth and respectively through the intermediate point between the medial canthus and the nasion, medial iris, medial canthus, on the right and left.

6) The inclination of the lines (1d, 1s) relative to the zeniths of the two upper central incisors (11, 21) indicates the horizontal deviation of the vertex of the parabola A to A1. The parabola obtained in this manner is the gingival parabola, proportionally reduced as a function of the ideal dimensions of the teeth.

D) Create a rectangle as follows:

The rectangle has known dimensions (obtained from known methods or software, such as by the method contained in U.S. Pat. No. 1,407,072 by the same applicant) or arbitrary inserted according to the discretion of the professional user.

The rectangle has the same height as the upper right central incisor (11) and its width is the maximum width of the same tooth.

The height of the rectangle is equal to the height of the clinical crown (hcc).

Figure 4:
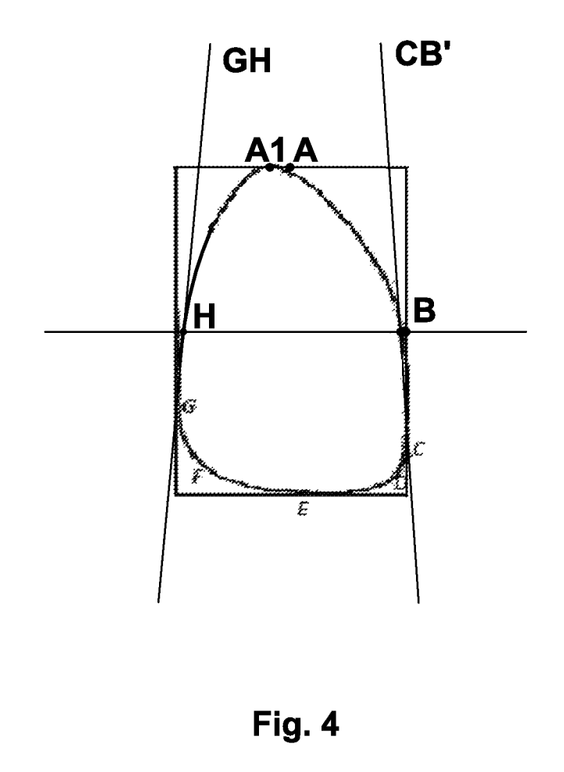
FIG. 4 shows an example of the construction of the tooth shape obtained following the determination of some points on a reference rectangle.
Figure 5:
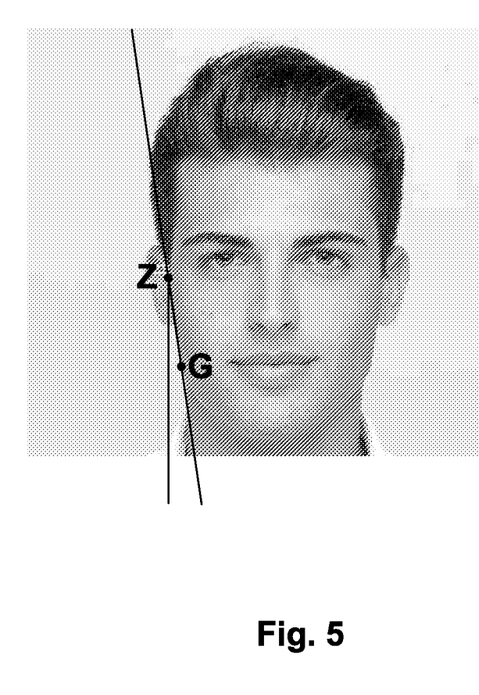
FIG. 5 shows a front view of the patient with no smile and closed mouth, on which the structure to determine the facial inclination angle (AIF) is indicated.

E) Determination of the following points on the rectangle, with reference to FIG. 4:

E is at the center of the lower horizontal side of the rectangle, that is, the vertical lower limit of the rectangle enclosing 11;

Determination of hcc*=hcc−13% hcc, where 13% is a fixed percentage in this method according to statistical data;

C is on the mesial surface of the rectangle, at a distance hcc* from the upper horizontal side of the rectangle;

G is on the distal segment, at a distance hcc−26% hcc from the upper horizontal side of the rectangle;

A is at the center of the upper horizontal side of the rectangle;

B is at a distance of hcc/2 from the upper segment;

Calculation of the position of H:

a) Measure the facial inclination angle (AIF), constructed by measuring the angle between the straight line passing through the zyghion (Z) and gonion (GN) on the same side of the face, and a vertical line passing through the zighion (Z);

b) Draw an oblique line (GH) on the rectangle, from point G upwards and toward the inside the rectangle, which forms an angle equal to the facial inclination angle (AIF) with the vertical side of the rectangle;

c) Intersect the oblique line (GH) with the horizontal line passing through B, where H is the point of intersection between the aforementioned oblique line (GH) and the aforementioned horizontal line passing through B;

d) The procedure shall be repeated from point C: on the rectangle, from point C, draw an oblique line (CB') upwards and toward the inside of the rectangle, which forms an angle equal to half of the facial inclination angle (AIF/2) with the vertical side of the rectangle; intersect the aforementioned oblique line (CB') with the horizontal line passing through B, determining a point B'.

F) Construction of the shape of the tooth (11):

The shape of the tooth is constructed on the frontal image of the face with the mouth closed and with no smile and is proportionally related to the ideal tooth to be constructed knowing the ideal dimensions obtained from another source. The calibration of the images enables the creation of a proportional image of the tooth.

G) Calculation of the gingival parabola:

The gingival parabola is obtained by transposing the parabola (P) drawn in steps B) and C) on the tooth (11).

Figure 6:
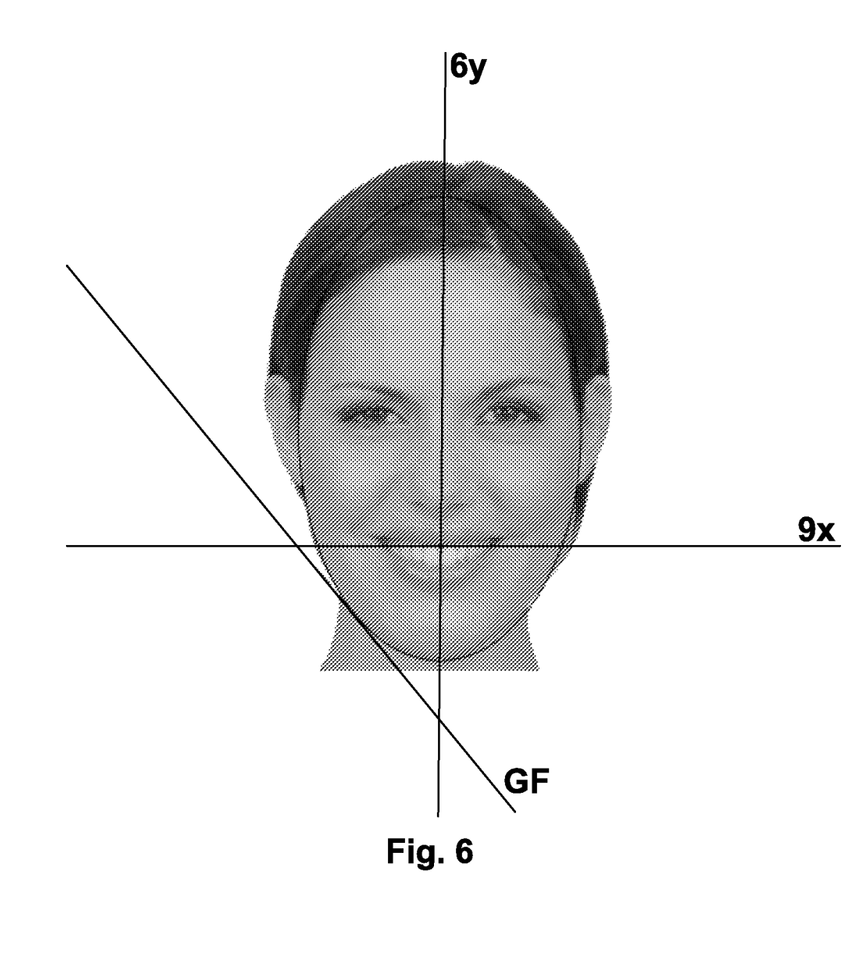
FIG. 6 shows the frontal image with smile and clenched teeth, on which the structure to determine the tangent line GF is indicated.

H) Calculation of the position of point F:

With reference to FIG. 6, draw a curve that approximates the contour of the face, and draw the tangent (GF) to that face contour curve at the point of intersection between the curve and the bisector of the angle formed by the horizontal line passing through the stomion (9x) and the vertical median line (6y).

On the rectangle, from point G, draw a line GF, where F is the intersection point between the line GF and the lower horizontal side of the rectangle.

Figure 7:
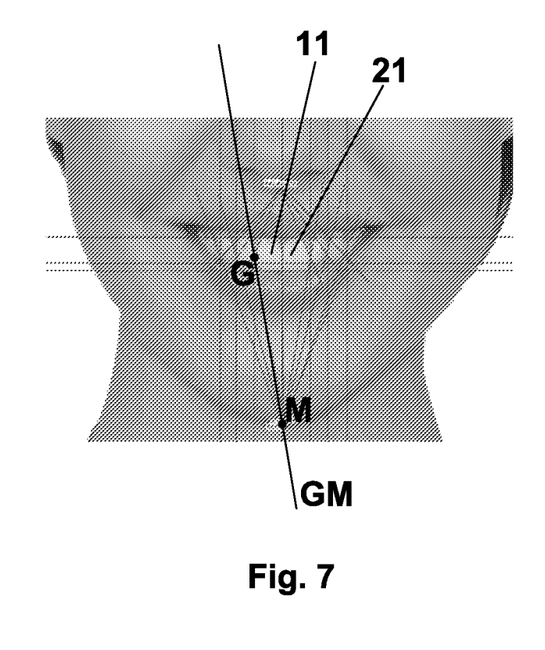
FIG. 7 shows that frontal image with smile and clenched teeth, on which the structure to determine the straight line GM is indicated.

I) Calculation of the position of point F1:

With reference to FIG. 7, considering the tooth in question, that is, the upper right central incisor (11), the oblique line (GM) passing through G and menton (M) is drawn.

On the rectangle, draw the line GM from point G, where F1 is the point of intersection between the line GM and the lower horizontal side of the rectangle.

L) Calculation of the position of point D:

Mirroring the procedure to determine point F, draw a line passing through C with the same inclination but opposite that of the line GF, and where the intersection between that line and the base of the rectangle determines point D.

M) Calculation of the position of point D1:

Mirroring the procedure to determine point F1, draw a straight line passing through C with the same inclination but opposite that of the line GM, where point D1 is determined by the intersection between that line and the base of the rectangle.

Figure 8:
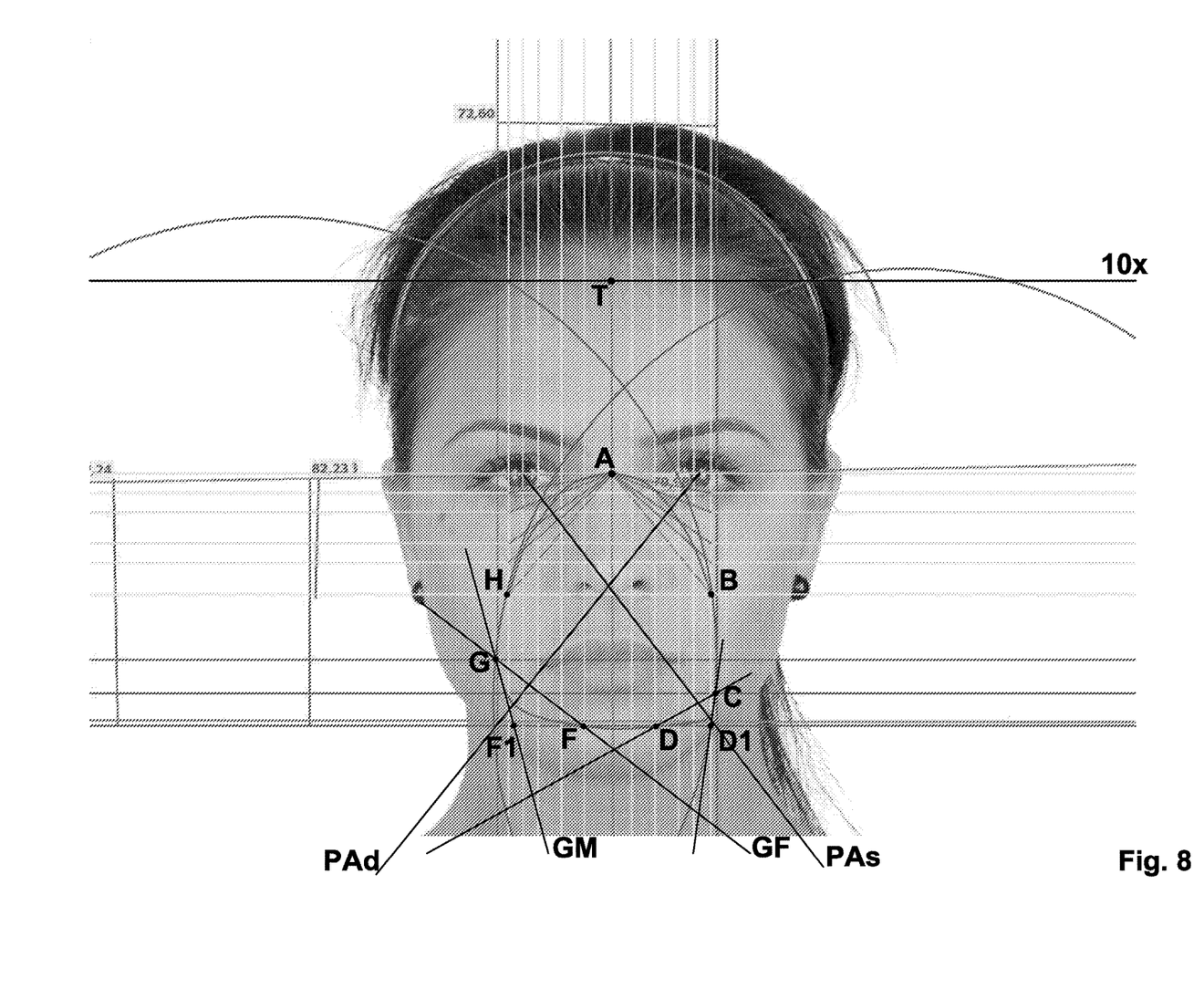
FIG. 8 shows the frontal image of the patient without a smile and with a closed mouth, on which the structure to plot the complete profile of the tooth (11) is indicated.

O) Construction of the parabolas corresponding to the distal and mesial incisal angles of the rectangle:

With reference to FIG. 8, the rectangle is essentially positioned on the patient's face image, wherein the directrix of the parabola with vertex on the distal or mesial angle of the rectangle is calculated by transferring on the drawing the inclination of the line (PAd, PAs) passing through the lower distal or mesial angle of the rectangle and the pupillary point of the opposite side of the face. The limits of the right or distal parabola are the segments GF and GF1 while the limits of the left or mesial parabola are the segments CD and CD1. The vertices of the parabolas are positioned so that their outer limits are as close as possible to the outer lines.

P) HG roundness:

With reference to FIG. 8, the curvature between H and G is established by the radius corresponding to the distance between the right and left zighion (Z).

Q) BC roundness:

The curvature between B and C is established by the radius corresponding to the distance between the right and left zighion (Z).

R) DEF roundness:

The curvature between D, E and F is determined as follows with reference to FIG. 8:

Draw the horizontal line (10x) passing through the trichion (T) and the horizontal line passing through the right and the left eurion. Determine their distance from each other. Proportionally reproduce the distance starting from E, in the vertical direction, to draw the curve DEF. Draw a horizontal line from the extreme point of that distance so as to intersect the mesial and distal parabolas. Draw an arc of a circle DEF coplanar with the inner limits of the parabolas.

S) Optimization:

If the HB segment is too small or too large and such as to result in the absence of continuity between the curves drawn, the segment must be shortened or lengthened until obtaining a regular curve.

The invention claimed is:

1. A method of determining and drawing an ideal individual shape of two upper front teeth (11, 21) of a patient, comprising:
    using a first image of a patient's face, in front view, non-smiling and with the patient's mouth closed;
    using a second image of the patient's face, in front view, smiling and with closed teeth;
    determining a front facial angle (AFF) of the patient's face, starting from the first image of the patient's face non-smiling and with the patient's mouth closed, wherein the front facial angle (AFF) is an angle defined between segments that are joined at a vertex at a level of a nasion (A) and pass through points of intersection (H, B) between a horizontal straight line (6x) passing through a nasal spine (N) and two vertical straight lines (1yd, 1ys) passing through distal points of irides, respectively a right and a left iris;
    drawing eleven vertical straight lines (1yd, 2yd, 3yd, 4yd, 5yd, 6y, 5ys, 4ys, 3ys, 2ys, 1ys) included between right and the left distal points of the irides on said first image of the patient's face, non-smiling and with the patient's mouth closed;
    drawing six horizontal straight lines (1x, 2x, 3x, 4x, 5x, 6x) on said first image of the patient's face non-smiling and with the patient's mouth closed, wherein a first straight line passes through pupils (1x) and a last straight line passes through a nasal spine (6x);
    joining a point on the nasion (A) with points of intersection between the two vertical straight lines (1yd, 1ys) passing through the distal points of the irides and five of said horizontal straight lines (2x, 3x, 4x, 5x) below a horizontal straight line passing through the pupils (1x) to obtain ten oblique lines;
    highlighting crossing points between said ten oblique lines and said vertical straight lines (1yd-6yd) and (1ys-6ys); and
    drawing a parabola with vertex at A and base at H and B, passing through the points highlighted in the previous step,
    wherein said parabola defines a shape of gingival margin.

2. The method according to claim 1, wherein said eleven vertical straight lines are the following:
    a vertical median line of the face (6y), passing through trichion (T), the nasion (A) and menton (M);
    a fourth right vertical line passing through a right medial canthus (4yd);
    a third right vertical line passing through a mesial point of the right iris (3yd);
    a second right vertical line passing through a right pupil (2yd);
    a first right vertical passing through the distal point of the right iris (1yd);
    a fourth left vertical line passing through a left medial canthus (4ys);
    a third left vertical line passing through a mesial point of a left iris (3ys);
    a second left line passing through the left pupil (2yd);
    a first left line passing through the distal point of the left iris (1ys); and
    two lines passing through median points of a segment between the nasion (A) and the right and left medial canthuses (5yd, 5ys).

3. The method according to claim 1, wherein said six horizontal straight lines (1x, 2x, 3x, 4x, 5x, 6x) are respectively spaced from one another by 16%, 16%, 26%, 16% o, 26% with respect to an interval included between extreme horizontal lines (1x, 6x).

4. The method according to claim 1, further comprising orienting the parabola to use said front view of the patient's face, smiling and with closed teeth, and further comprising the following steps:
    positioning one of the eleven vertical straight lines to be a vertical median line (6y);
    drawing a horizontal straight line passing through a glabella (7x), the pupils (1x) and a right and a left chelion (8x);
    drawing oblique lines with vertex (GL) in a point of intersection between the horizontal straight line passing through the glabella (7x) and the vertical median line (6y), said oblique lines passing through the right and the left chelion (Kd, Ks);
    drawing median lines of upper front teeth that affect a smile area; and
    drawing straight lines (1d, 2d, 3d, 4d, 1s, 2s, 3s, 4s) passing through the upper front teeth and, respectively, through an intermediate point between a medial canthus and the nasion, a medial point of the left and respectively the right iris, the medial canthus,
    wherein an inclination of two of the straight lines (1d,1s) that are related to zenith positions of two upper central incisors indicates a horizontal shift of the vertex of the parabola.

5. The method according to claim 4, further comprising:
    creating a rectangle having a height equal to a clinical crown (hcc) of a tooth (11) and a width equal to a maximum width of the same tooth;
    locating the following points on said rectangle:
        at least one point (E) at a center of a lower horizontal side of the rectangle,
        at least one point (C) at a distance hcc*=hcc−13% hcc from an upper horizontal side of the rectangle,
        at least one point (G) on a distal side of the rectangle at a distance hcc−26% hcc from the upper horizontal side of the rectangle,
        at least one point (A) at a center of an upper horizontal side of the rectangle, and
        at least one point (B) at a distance hcc/2 from an upper segment of the rectangle;
    calculating a position of point H, by:

measuring a facial inclination angle (AIF) constructed by measuring an angle between a straight line passing through a zyghion (Z) and a gonion (GN) of the same side of the face and a vertical straight line passing through the zighion (Z);

drawing on the rectangle, from said at least one point G, an oblique line (GH) directed upwards and towards an inside of the rectangle, which forms, together with a vertical side of the rectangle, an angle that is equal to the facial inclination angle (AIF);

intersecting said oblique line (GH) with a horizontal line passing through said at least one point B, where H is a point of intersection between said oblique line (GH) and said horizontal line passing through said at least one point B; and calculating a position of point C by:
  drawing on the rectangle, from the at least one point C, an oblique line (CB') directed upwards and towards the inside of the rectangle, which forms, together with the vertical side of the rectangle, an angle that is equal to half the facial inclination angle (AIF/2), and
  intersecting said oblique line (CB') with a horizontal line passing through B, determining a point B',
wherein said parabola (P) is drawn between said points A, H and B, and wherein the vertex of the parabola is moved from A to A1 according to said horizontal shift.

6. The method according to claim 5, further comprising:
calculating a position of point F on said rectangle by:
  drawing a curve reproducing a contour of the face on said first image of the face in front view, smiling and with closed teeth,
  drawing a tangent (GF) to said curve of the face contour at a level of a point of intersection between said curve and a bisector of an angle formed by a horizontal straight line passing through a stomion ($9x$) and a vertical median line ($6y$), and
  on said rectangle, from said at least one point G, drawing said tangent GF, where F is a point of intersection between the tangent GF and the lower horizontal side of the rectangle;

calculating a position of point F1 on said rectangle by:
  drawing, on said image of the face in front view, smiling and with closed teeth, an oblique line (GM) passing through said at least one point G of the tooth (11, 21) and a menton (M), and
  drawing, on said rectangle, said oblique line GM from said at least one point G, where F1 is a point of intersection between the oblique line GM and the lower horizontal side of the rectangle;

calculating a position of point D, drawing a straight line passing through the at least one point C with an inclination equal to and opposite the inclination of said tangent GF, wherein an intersection between said oblique line and a base of the rectangle determines point D; and calculating a position of point D1, drawing a straight line passing through the at least one point C with an inclination equal to and opposite that of said straight line GM, wherein an intersection between said straight line and the base of the rectangle determines point D1.

7. The method according to claim 6, further comprising constructing mesial and distal parabolas corresponding to distal and mesial incisal angles of the rectangle, based on said mesial and said distal parabolas the rectangle being substantially transferred on the first image of the patient's face, non-smiling and with the mouth closed, wherein a directrix of the mesial and the distal parabolas with vertex on the distal or mesial angle of the rectangle is calculated by transferring on a drawing an inclination of a straight line (PAd, PAs) passing through a lower distal or mesial angle of the rectangle and a pupillary point of an opposite side of the face, so that limits of a right or distal parabola comprise segments GF and GF1 and limits of a left or mesial parabola are segments CD and CD1.

8. The method according to claim 7, further comprising constructing curved sections HG and BC, which are a first curve that joins said points H and G and a second curve that joins said points B and C, by tracing therebetween an arc of a circle with a radius corresponding to a distance between a right and a left zighion (Z).

9. The method according to claim 7, further comprising constructing a curved section DEF, which is a curve that joins points D, E and F by:
  drawing a first horizontal straight line (10$x$) passing through a trichion (T) and a second horizontal straight line passing through a right and a left eurion, determining a distance between the first horizontal straight line (10$x$) passing through the trichion (T) and the second horizontal straight line passing through the right and the left eurion;
  proportionally reproducing a distance starting from E, in the vertical direction, and wherein a horizontal straight line is drawn from an extreme point of said distance starting from E and intersects said mesial and said distal parabolas; and
  drawing an arc of a circle DEF coplanar with inner ends of the mesial and distal parabolas.

10. The method according to claim 6, further comprising optimizing by checking a length of a segment between the point of intersection H and a point of intersection B, wherein if said segment is too small or too large and such as to result in an absence of continuity between drawn curves, said segment the points of intersection H and B is shortened or lengthened until obtaining a continuous curve.

* * * * *